(12) United States Patent
Oishi et al.

(10) Patent No.: US 8,486,100 B2
(45) Date of Patent: Jul. 16, 2013

(54) GUIDE TUBE HAVING BALLOONS FOR PUNCTURE

(75) Inventors: Hideto Oishi, Tokyo (JP); Yukihiko Sakaguchi, Akita (JP)

(73) Assignees: Sumitomo Bakelite Co., Ltd., Tokyo (JP); Hideto Oishi, Tokyo (JP)

( * ) Notice: Subject to any disclaimer, the term of this patent is extended or adjusted under 35 U.S.C. 154(b) by 222 days.

(21) Appl. No.: 12/747,026

(22) PCT Filed: Dec. 18, 2007

(86) PCT No.: PCT/JP2007/074337
§ 371 (c)(1),
(2), (4) Date: Aug. 27, 2010

(87) PCT Pub. No.: WO2009/078097
PCT Pub. Date: Jun. 25, 2009

(65) Prior Publication Data
US 2010/0318094 A1      Dec. 16, 2010

(51) Int. Cl.
*A61M 29/00* (2006.01)

(52) U.S. Cl.
USPC ............................ 606/191; 600/115; 600/116

(58) Field of Classification Search
USPC .................. 604/27, 48, 96.01, 97.01, 97.03, 604/98.01, 101.01–101.02, 103.01, 103.06; 606/108, 191–192, 196, 198; 600/115–116
See application file for complete search history.

(56) References Cited

U.S. PATENT DOCUMENTS

| | | | | |
|---|---|---|---|---|
| 4,384,584 | A | | 5/1983 | Chen |
| 5,360,403 | A | * | 11/1994 | Mische .................. 604/101.02 |
| 5,840,066 | A | * | 11/1998 | Matsuda et al. ......... 604/102.02 |
| 6,554,842 | B2 | * | 4/2003 | Heuser et al. ................. 606/108 |
| 6,682,536 | B2 | * | 1/2004 | Vardi et al. ..................... 606/108 |
| 6,685,671 | B1 | | 2/2004 | Oishi et al. |
| 6,746,465 | B2 | * | 6/2004 | Diederich et al. ............. 606/192 |
| 6,830,559 | B2 | * | 12/2004 | Schock .................... 604/103.06 |
| 2006/0241345 | A1 | | 10/2006 | Oishi et al. |

FOREIGN PATENT DOCUMENTS

| | | |
|---|---|---|
| WO | 99-36120 A1 | 7/1999 |
| WO | 2004-067080 A1 | 8/2004 |
| WO | 2007-018472 A1 | 2/2007 |

OTHER PUBLICATIONS

International Search Report of PCT/JP2007/074337, Mailing Date of Feb. 26, 2008.

* cited by examiner

*Primary Examiner* — Katherine Dowe
*Assistant Examiner* — Kendra Obu
(74) *Attorney, Agent, or Firm* — Westerman, Hattori, Daniels & Adrian, LLP

(57) ABSTRACT

To provide a guide tube equipped with a balloon for puncture, devised to ensure a deeper level of puncture when the balloon is punctured with a puncture needle, in order to safely and reliably ensure a route for percutaneous approach to the inside of the body.

10 Claims, 3 Drawing Sheets

GUIDE TUBE HAVING BALLOONS FOR PUNCTURE

TECHNICAL FIELD

The present invention relates to a guide tube equipped with a balloon for puncture, which is a tool intended to safely and reliably ensure a route for percutaneous approach to the inside of a body, and employs, as a target, a balloon which does not immediately burst when punctured, for example, with a puncture needle, wherein an inner balloon is formed in such a manner that an endoscope can be inserted into a tube holding the balloon, and used.

Conventionally, Percutaneous Endoscopic Gastrostomy (PEG), which is one of endoscopic surgeries for forming fistulas on the stomach lumen and on the skin surface of the abdominal wall using an endoscope has been developed in 1979 especially as an enteral nutrition administration method by a pediatric surgeon, Gaudert and an endoscopic surgeon, Ponsky (for example, see Patent Document 1), and several procedures based on this technique have been further developed, and are each spreading widely.

However, these techniques cannot be used, or are hard to use, in cases such as "cases of retention of ascites in a large amount" and "cases where the liver or transverse colon is positioned between the stomach and the abdominal wall" and "anamnestic cases of stomach surgeries" due to the puncture of the gastric wall/abdominal wall.

Further, as for a method for transnasally placing a tube in the stomach, long-term placement may increase pains of the nostril, nasal cavity and pharynx and may form an ulcer in the nostril, thereby making it difficult to maintain the placement, in some cases. Further, even pneumonia may develop together due to difficulty in expectoration of sputum, in some cases. Thus, this method is not preferable from these QOL viewpoints.

On the other hand, a method for forming a cervical esophageal fistula under X-ray fluoroscopy was developed by Nakano et al. in 1993. The placement technique employed in this method involves transnasally inserting a tube equipped with a balloon into the esophagus, injecting a contrast agent into the balloon at the cervical esophagus to expand the inner cavity of the cervical esophagus, then percutaneously puncturing the cervical esophagus under X-ray fluoroscopy to form a cervical esophageal fistula, and placing a nutrition tube therein. This placement technique is simple, less invasive and less painful to patients, and useful in long-term nutrition management.

This method, however, involves puncturing only under X-ray fluoroscopy, and thus might be risky in view of the anatomical structure of the cervical part. In this method, while an indwelling bladder foley catheter is used as the tube equipped with a balloon, it is visually recognized, based on the rupture of the balloon, whether a puncture needle has reached the inner cavity of the esophagus at the time of puncturing. Therefore, there was a possibility that the esophagus wall would be damaged by a needle tip end or that the needle is inserted only into a shallow site and thus would come off from the esophagus wall, after rupture of the balloon.

Thus, in 1997, Oishi et al., who are also inventors of the present invention, have improved the method for forming a cervical esophageal fistula under X-ray fluoroscopy by Nakano et al., and then have invented a method for safely and reliably puncturing a balloon with a puncture needle while confirming the balloon position using an ultrasonic probe from the outside of the body as a method for puncturing a balloon of a balloon catheter (for example, see Non-Patent Documents 1 and 2).

Further, the inventors of the present invention have further improved the above method for forming a cervical esophageal fistula to form a balloon of a balloon catheter to be punctured, which does not immediately burst even upon puncture of the balloon, and also to combine the above method with dedicated introduction tools (for example, see Patent Document 2) in order to aim at bed-side implementation of the method without use of an X-ray imaging machine.

Patent Document 1: Japanese Patent Application National Publication (Laid-Open) No. 6-503243
Patent Document 2: International Publication No. WO99/36120
Non-Patent Document 1: Oishi, "Percutaneous/Trans-Cervical Esophageal Gastrostomy, Adaptation and Usefulness Thereof," Journal of Japan Surgical Society, 1997
Non-Patent Document 2: Oishi, "Percutaneous/Trans-Cervical Esophageal Gastrostomy, Tricks and Sub-Damages thereof," Journal of Japanese Society of Gastroenterological Surgery, 1997

DISCLOSURE OF INVENTION

Problem to Be Solved by Invention

The present invention has been made in light of the actual situation of the above-described guide tube equipped with a balloon for puncture, and an object thereof is to provide a guide tube equipped with a balloon for puncture, devised to ensure a deeper level of puncture when the balloon is punctured with a puncture needle, in order to safely and reliably ensure a route for percutaneous approach to the inside of the body.

Means for Solving Problem

Namely, the present invention relates to a guide tube equipped with a balloon for puncture, including a main body tube equipped with a balloon on its tip end-side surface, the tube having a main lumen for insertion of an endoscope, which penetrates from the rear end to the tip end, and a sub lumen brought in gas/liquid communication with the inside of the balloon, the main lumen being provided, at its rear end, with an endoscope insertion part, and the sub lumen being provided, at its rear end, with connectors for inflating and contracting operations of the balloon, wherein the balloon on the tip end-side surface is used as an outer balloon, a needle through hole, through which a puncture needle sufficiently passes, is formed in a wall surface of the main body tube located inside the outer balloon, the hole is blocked air-tightly with an inflatable sheet material, and the sheet material is provided as an inner balloon, the inner balloon being so formed that, upon inflation of the outer balloon, the inner balloon inflates and projects from the needle through hole toward the inside of the main lumen due to the internal pressure of the outer balloon, so that the tip end of the puncture needle can be pierced into the inflating and projecting part.

(2) In the guide tube equipped with a balloon for puncture according to the present invention, while the outer balloon and the inner balloon are desirably formed of the same material in the above configuration, the same material is not necessarily used to form the balloons.

(3) The elongate hole for insertion of the puncture needle desirably has a size of about 10 mm×20 mm.

(4) As regards the through hole, it is preferable to provide a marking for identifying the position of the hole on the outer periphery wall of the main body tube on a line along the length direction of the main body tube including the hole. The marking may be provided in either pattern, at the front side of the main body tube or over an area from the front side to the vicinity of the hole.

(5) Further, a reinforcing pipe is mounted on the inner surface of the main lumen provided with the elongate hole in the main body tube. The reinforcing pipe is intended to prevent the deformation or collapse of the lumen provided with the elongate hole for needle insertion when the outer balloon is inflated.

(6) The balloon for puncture recited in any one of the above items (1) to (4) is characterized in that the outer balloon has the following material properties: a thickness of 0.01 mm to 1 mm, a tensile strength of 8 MPa to 25 MPa, a 100% modulus of 3 MPa to 6 MPa, an elongation of 300% to 460%, and a balloon internal pressure of 2.8 psi to 75 psi, and that the inner balloon has material properties which are identical with those of the outer balloon, or has such material properties that the inner balloon is easier to inflate than the outer balloon.

(7) The guide tube according to any one of the above items (1) to (5) is characterized in that the main body tube has transparency ensuring visual recognition of the inside of the outer balloon from the endoscope.

(8) The guide tube according to any one of the above items (1) to (6) is characterized in that a balloon attachment part located at least at the tip end side of the main body tube is mounted to be arranged inside the balloon with respect to the longitudinal direction of the outer balloon.

(9) The guide tube according to any one of the above items (1) to (7) is characterized in that the lumen for endoscope insertion is equipped, its rear end, with a membrane-like seal member having a slit or a hole.

EFFECT OF INVENTION

The guide tube equipped with a balloon for puncture according to the present invention is used so that a puncture needle can be pierced into a balloon more deeply when the balloon is punctured with the puncture needle. Thus, the guide tube is quite convenient in safely and reliably forming percutaneous routes for various purposes in all the hollow organs (such as esophagus, stomach, bile duct, pancreatic duct, intestine, ureter and bladder).

BEST MODE FOR CARRYING OUT INVENTION

Next, the present invention will be specifically described, with reference to the drawings.

FIG. 1 is a sectional side view of a conventional guide tube equipped with a balloon for puncture (hereinafter, simply referred to as the "guide tube"). FIG. 2 is a schematical view showing a method for using the guide tube shown in FIG. 1. FIG. 3 is a sectional side view of the guide tube as one Example of the present invention. FIG. 4 is a sectional side view showing an enlarged tip end of the guide tube as one Example of the present invention. FIG. 5 is a right-side sectional view of FIG. 4, and FIG. 6 is a flat sectional view of FIG. 4. FIG. 7 is a sectional side view of an enlarged tip end part, showing the state where a puncture needle is inserted when the guide tube as one Example of the present invention is inflated. FIG. 8 is a right-side sectional view of FIG. 7.

First, one example of conventional endoscope-insertion type guide tubes equipped with a balloon for puncture will be described with reference to FIGS. 1 and 2. A conventional guide tube includes a main body tube 1, a balloon 2, a connector 3, a membrane-like seal part 4 for endoscope insertion, a main lumen 5 for endoscope insertion, a sub lumen 6 and a balloon attachment part 7, as shown in FIG. 1.

The main body tube 1 shown in FIG. 1 is a thin tube having one or more inner cavities. One of the inner cavities is the sub lumen 6 for balloon inflation, of which the tip end is blocked and has a side hole 6a which opens to a balloon inner cavity. The main lumen 5 for endoscope insertion is formed to have a thickness approximately equivalent to that of an endoscope 20 used and an appropriate length, with consideration for the physical size of a patient, insertion site, and the like. Further, the main body tube 1 has appropriate flexibility and elasticity at normal room temperature and body temperature, and the commonly used materials therefor include synthetic resins such as soft vinyl chloride resins, polyurethane resins and silicone rubbers. In short, any material can be used so long as the material has such transparency that one can visually recognize the inside of the balloon by means of the endoscope.

Next, as one example of methods of using the conventional guide tube described with reference to FIG. 1, a method for ensuring a percutaneous insertion route from the cervical part to the esophagus will be described with reference to FIG. 2. As shown in FIG. 2, the endoscope 20 for the upper digestive organs, bronchial tubes or any other applications is inserted into the main lumen 5 for endoscope insertion of the guide tube, and they are orally inserted into a site passing over the entrance part of the esophagus in the state where the endoscope 20 projects from the tip end of the guide tube. Then, the guide tube is inserted along the endoscope 20, and, at a position where the balloon 2 has passed over the entrance part 23 of the esophagus, physiological saline or the like is injected from the connector 3 preliminarily connected to a syringe 21 or the like to inflate the balloon 2. Further, the endoscope 20 is pulled backward to ensure a broad puncture site, and the position of the balloon 2 is confirmed by means of an ultrasonic probe contacted with the cervical part from the body surface.

The ultrasonic probe is strongly pushed to establish the state where the thyroid, trachea, artery, vein and the like are shifted to the right/left side with respect to the balloon 2, and, in that state, a puncture needle 22 is pierced toward the balloon 2. It is confirmed, in an endoscopic image and an ultrasonic image, that the balloon 2 does not burst or contract at the moment when the balloon is punctured with the puncture needle 22, and that the tip end of the needle 22 is surely located within the balloon 2.

After the above operations, a guide wire (not shown) is inserted in a necessary quantity from the terminal end of the puncture needle 22 for the removal of the puncture needle 22. While pushing the endoscope 20 and balloon 2 for puncture and directing the guide wire toward the stomach side, the puncture needle 22 is detached from the inside of the balloon 2. The physiological saline or the like within the balloon 2 is sucked by means of the syringe 21 to cause this balloon 2 to contract, and the endoscope 20 is pulled back to the upper part of the esophagus. A dilator with a sheath (not shown) is inserted from the terminal end of the guide wire to expand the puncture side, with visual recognition by means of the endoscope 20. Then, only the dilator is removed to ensure a route to the inside of the esophagus. By virtue of the thus-ensured route, an appropriate catheter is subsequently inserted.

In the conventional guide tube described with reference to FIGS. 1 and 2, when the balloon 2 is punctured with the puncture needle 22, once the tip end of the needle 22 is contacted with the surface of the sub lumen 6 within the balloon 2 or of the lumen 5 for endoscope insertion, the needle cannot be pierced any more. Thus, the puncture depth is shallow and has a limit, and the puncture needle 22 may possibly come off from the balloon 2.

Then, according to the present invention, the balloon 2 of the main lumen 5 for endoscope insertion is used as an outer balloon, and, at a site positioned inside the outer balloon 2, an elongate hole 10 having a size of about 10 mm×20 mm has been formed as a needle through hole through which the puncture needle 22 sufficiently passes, and an inflatable sheet material capable of blocking this elongate hole 10 air-tightly has been provided as an inner balloon 9. By virtue of this configuration, when a liquid is injected from the sub lumen 6 into the outer balloon 2 so that the balloon 2 inflates, the inner balloon 9 inflates and projects from the elongate hole 10 toward the inside of the main lumen 5 due to the internal pressure of the balloon (see FIGS. 7 and 8). As a result of this, when the outer balloon 2 is punctured with the puncture needle 22, the tip end 22a of the puncture needle 22 can pass through the elongate hole 10, and can be pierced into the inner balloon 9 inflating and projecting to the inside of the hole 10. Here, the outer balloon 2 does not immediately burst, and firstly contracts by suction of the liquid within the balloon 2, and thus one can endoscopically and ultrasonically recognize the state where the tip end 22a of the puncture needle 22 is located within the inflating and projecting inner balloon 9. The puncture needle 22 can be inserted into a deeper site, thereby preventing the needle 22 from coming off from the outer balloon 2 and ensuring the inner cavity until the outer balloon 2 contracts.

In the meantime, the tip end of the main body tube 1 is, of course, subjected to chamfering or the like to improve the insertability of the tube into the body, and desirably has an obliquely cut shape, not an orthogonally cut shape, though not shown, in order to improve the insertability.

Next, a specific example of the guide tube including a main lumen 5 for endoscope insertion according to the present invention will be described with reference to FIGS. 3 to 7. As illustrated in FIG. 3, the guide tube of the present invention includes a main body tube 1, a balloon 2, a connector 3, a membrane-like seal part 4, a main lumen 5 for endoscope insertion, a sub lumen 6, and a balloon attachment part 7. While the guide tube is similar in this regard to the conventional guide tube shown in FIG. 1, the balloon 2 described above is referred to as an outer balloon in the present invention.

The main body tube 1 shown in FIG. 3 is formed of a thin tube, and includes the main lumen 5 for endoscope insertion which is formed to have forms, such as an inner diameter, and properties such that an endoscope 20 penetrating from its tip end to its rear end can be inserted/pulled out, and the sub lumen 6 having a blocked tip end and a side hole 6a opened to the inner cavity of the outer balloon 2, in which the rear end of the main body tube 1 communicates with the connector 3 to allow a fluid for inflation of the balloon to flow in/out of the inner cavity of the balloon 2.

In the meantime, this guide tube is also similar to the previously-described example also in the chamfered shape, obliquely cut shape and the like of the tip end of the main body tube 1 shown in FIG. 3 in order to improve the insertability.

While the main body tube 1 described above is desirably as small in outer diameter as possible, while ensuring an inner diameter enough to insert the endoscope used, namely, thin, the main body tube 1 is determined to have an appropriate dimension to prevent the blocking of the inner cavity caused by bending. Therefore, one of desirable working examples is to use a composite tube as the main body tube 1 and to embed a resin, a metal mesh or the like therein. The length of the main body tube 1 is arbitrarily determined depending on the target site. Further, the main body tube 1 has appropriate flexibility and elasticity at normal room temperature and body temperature. Normally, synthetic resins such as soft vinyl chloride resins, polyurethane resins and silicone rubbers are suitably used as the material for forming the main body tube 1, but the usable materials are not limited thereto in the present invention.

Next, the outer periphery or inner cavity of the main body tube 1 of the present invention is also desirably subjected to lubricative treatment, and practical examples of the treatment include coating of various hydrogels, in addition to fluororesin coating and kneading of a silicone oil into the material, and collagen, polyvinylpyrrolidone, polyacrylamide and the like are preferably used as the hydrogels with consideration for the toxicity to the human body. Methods that can be utilized to fix these substances onto the main body tube 1 include a method including coating a catheter with these hydrogels previously prepared as solutions followed by crosslinking with glutaraldehyde, a method including coating a catheter with monomers of these hydrogels followed by crosslinking with a polymerization initiator, and a method including coating the main body tube 1 with a solution of a hydrogel modified with a photoactive crosslinking agent and then fixing it by light irradiation. Further, the main body tube 1 is desirably formed of a material having such transparency that one can visually recognize the inside of the balloon 2 under the endoscope.

The outer balloon 2 is formed to have a length ranging from 1 cm to 20 cm, an inflation diameter ranging from 5 mm to 200 mm and a thickness ranging from 0.01 mm to 1 mm depending on the insertion site. For example, the balloon is formed to have a thickness, for example, of about 0.1 mm to 0.3 mm to maximally prevent the balloon from being bulky for intranasal insertion, to have a length of about 3 cm to 10 cm and an inflation diameter of about 30 mm for the esophagus, and to have a length of about 5 cm to 20 cm and an inflation diameter of about 200 mm for the stomach.

A synthetic resin having a JIS-A hardness of 20 to 80, a tensile strength of 8 MPa to 25 MPa, a tear strength of 20 kg/cm to 60 kg/cm, a 100% modulus of 3 MPa to 6 MPa, an elongation of 300% to 460% and a balloon internal pressure of 2.8 psi to 75 psi is normally selected as the material for forming the outer balloon 2. Although a soft vinyl chloride resin, a polyurethane resin, a silicone rubber and the like are suitably used as the material, the usable materials are not limited thereto. Polyethylene, polyester, natural rubber latex and the like may be used.

It should be noted that, when the outer balloon 2 is formed of a silicone rubber, a natural rubber or the like, there is a possibility that the outer balloon 2 may burst, due to its elasticity, at the moment when the outer balloon 2 is punctured with the puncture needle. Therefore, ingenious devices of forming a nylon mesh or the like on the outer balloon 2 by impregnation or lamination, and coating the front or back surface or many layers of the balloon 2 with a synthetic resin, may be employed in some cases, in order to prevent the balloon 2 from bursting as soon as the balloon 2 is punctured with the puncture needle.

As one example, when the outer balloon 2 for oral insertion into the esophagus is made of a soft vinyl chloride resin, a material having a hardness of 60, a tensile strength of 16 MPa, a tear strength of 45 kg/cm, a 100% modulus of 4.5 MPa and an elongation of about 400% is selected so that the outer balloon 2 is formed to have a thickness of about 0.1 mm to 0.3 mm and an outer diameter which is about ⅔ of the desired inflation diameter. Thus, an appropriate internal pressure is attained, due to which the liquid for inflation of the balloon gradually flows out of a needle base, without momentary bursting of the outer balloon 2 when the puncture needle is pierced thereinto and an inner needle is withdrawn, after the inflation of the outer balloon 2 up to the desired inflation diameter. The outer balloon 2 is molded into a desired shape by molding means such as blow molding, dip molding, extrusion molding, compression molding and the like.

As regards the method for attaching the outer balloon 2, it is desirable to reduce the protrusion length thereof from the tip end of the endoscope as much as possible, as described above. At least, the balloon attachment part 7 at the tip end side with respect to the main body tube 1 is desirably folded back and attached to be arranged inside this outer balloon 2, and adhesion, welding and other means are selected for the attachment thereof. This can reduce damages of tissues around the insertion site.

The endoscope may be inserted into any site so long as the endoscope insertion site satisfies the insertion operability with the endoscope 20 depending on the selected material for the main body tube 1. For example, a soft vinyl chloride resin may be selected as the material for the main body tube 1 to prevent the puncture needle 22 from passing therethrough, and a silicon rubber may be selected as the endoscope insertion site due to its flexibility. Namely, it is also desirable to select different materials.

The sub lumen 6 is intended to connect the outer balloon 2 and the connector 3 in a gas/liquid circulating manner to allow a liquid for inflation/contraction of the balloon 2 to circulate. The material used for the sub lumen 6 is not especially limited so long as the material has flexibility and sufficient strength, and a soft vinyl chloride resin, a polyurethane resin, a silicone rubber and the like are suitably used.

In the present invention, a slit-like elongate hole 10 penetrating to the main lumen 5 for endoscope insertion has been provided at a site where the outer balloon 2 is attached, specifically, within a range enveloped in the outer balloon 2, at the tip end side of the main body tube 1, and this elongate hole 10 has been air-tightly blocked with an inflatable sheet material so that this sheet material has been used as an inner balloon 9. The sheet material shown has a rectangular shape which is larger than the elongate hole 10.

In the present invention, a cylindrical sheet material covering the entire periphery of the main body tube 1 can also be used as the sheet material serving as the inner balloon 9. When the cylindrical sheet material is used, a communication hole which communicates with the side hole 6a at the tip end of the sub lumen 6 is provided. While the quality and properties of the sheet material used as the inner balloon 9 are desirably similar to those of the outer balloon 2, the inner balloon 9 may be formed of a material having such a property that the inner balloon 9 is easily inflatable as compared with the outer balloon 2. The materials for the inner balloon 9 are not limited to the examples indicated above.

Further, in the present invention, in order to identify the position (which has the same meaning as the position on the outer periphery of the main lumen 5 for endoscope insertion) of the elongate hole 10 over which the inner balloon 9 is provided in the circumferential direction of the main body tube 1, a marking 11 is provided on a straight line including the hole 10 in the length direction of the main body tube 1 (or lumen 5). This marking 11 may be positioned either at the front side of the main body tube 1 or over an area from the front side to the vicinity of the elongate hole 10 (see FIG. 6).

When a liquid for inflating the outer balloon 2 is injected into the balloon 2 by means of a syringe 21 connected via the connector 3 to the rear end of the main body tube 1 in the state where the inner balloon 9 described above is provided, the outer balloon 2 inflates outwardly. At this time, the inner balloon 9 to which the internal pressure of the inflating outer balloon 2 is applied inflates and projects toward the inside of the main lumen 5 for endoscope insertion from the elongate hole 10 (see FIG. 7).

In the present invention, in order to identify the position of the part of the inner balloon 9 inflating and projecting toward the inside of the lumen 5, i.e., the position of the elongate hole 10, on the inner periphery of the main body tube 1 (or the lumen 5), a marking 11 is provided on an extension of the elongate hole 10 along the length direction of the main body tube 1. This marking 11 may be positioned either at the front side of the main body tube 1 or over an area from the front side to the vicinity of the elongate hole 10.

By the above operations, a space where the tip end 22a of the puncture needle 22 can go into the main lumen 5 for endoscope insertion, i.e., the part of the inner balloon 9 inflating and projecting toward the inside of the lumen 5 is formed inside the outer balloon 2 facing the inner balloon 9 in an aspect as illustrated in FIGS. 7 and 8.

Since the present invention adopts such a configuration that the elongate hole 10 is formed in the main body tube 1 positioned inside the outer balloon 2, and that the hole 10 is blocked with the inner balloon 9, a "cutout" due to the elongate hole 10 would be formed on the "cylindrical cross section" of the main body tube 1. This "cutout," due to its "cutout effect," may possibly cause deformation or collapse of the cross section of the main body tube 1 when a liquid is injected into the outer balloon 2 to inflate the balloon 2 and the internal pressure of the balloon 2 is applied to the entire periphery of the lumen 5.

Thus, the present invention may sometimes adopt such a configuration that a reinforcing pipe 8 made of a thin metal or a hard synthetic resin and just fitted to the inner surface of the main lumen 5 for endoscope insertion formed with the elongate hole 10 is arranged on the inner surface thereof, in order to prevent the above-described deformation or collapse. Here, the inner surface of the pipe 8 may be arranged to coincide with the inner surface of the main lumen 5, or may be a pipe 8 made of a mesh cloth through which the puncture needle 22 cannot pass.

Here, the connector 3 is connected to the syringe to ensure injection of the liquid for inflation of the outer balloon 2, and thus must be of luer taper. However, valve members (for example, one-way valve, two-way valve and three-way valve) and, additionally, connectors having a lock-type terminal end may optionally be used. Although the materials for the connector 3 and the valve member are not especially limited, it is effective to use synthetic resins such as hard vinyl chloride resins, polycarbonate resins and ABS resins.

Next, as one example of the method for using the guide tube according to the present invention described with reference to FIGS. 3 to 8, a method for ensuring a percutaneous insertion route from the cervical part to the esophagus will be described. This method is basically identical with the method for using the conventional guide tube (FIG. 1) previously described with reference to FIG. 2.

As shown in FIG. 2, the endoscope 20 for use in the upper digestive organs, bronchial tubes or any other applications is inserted into the main lumen 5 for endoscope insertion of the guide tube, and they are orally inserted into a site passing over the entrance part of the esophagus in the state where the endoscope 20 is projected from the tip end of the guide tube. Then, the guide tube is inserted along the endoscope 20, and, at a position where the outer balloon 2 has passed over the entrance part 23 of the esophagus, physiological saline or the like is injected from the connector 3 preliminarily connected to a syringe 21 or the like to inflate the outer balloon 2. Then, the endoscope 20 is pulled backward to ensure a broad puncture site, and the position of the outer balloon 2 is confirmed by means of an ultrasonic probe contacted with the cervical part from the body surface.

The ultrasonic probe is further strongly pushed to establish the state where the thyroid, trachea, artery, vein and the like are shifted to the right/left side with respect to the outer balloon 2, and, in that state, a puncture needle 22 is pierced toward the outer balloon 2. In the piercing of the puncture needle 22, puncture can be carried out using the marking 11 as an index so that a needle tip 22a is not deviated from the elongate hole 10. It is confirmed, in an endoscopic image and an ultrasonic image, that the outer balloon 2 does not burst or contract at the moment when the outer balloon 2 is punctured with the needle 22, and that the tip end 22a of the needle 22 is surely located within the outer balloon 2.

At this time, in the guide tube according to the present invention, the space wherein the puncture needle 22 can enter is formed within the main lumen 5 through the elongate hole 10 due to the outward inflation of the outer balloon 2 and the inflation and projection of the inner balloon 9 provided over the elongate hole 10 within the balloon 2. Thus, it is possible to carry out the operation of inserting the puncture needle 22 into a deeper site than ever before. Even if the inner balloon 9 is punctured with the puncture needle 22, the balloon 9 does not burst at once. Thus, there is no risk that an endoscopic image or ultrasonic image cannot be taken immediately.

Then, a guide wire (not shown) is inserted in a necessary quantity from the terminal end of the puncture needle 22 for the removal of the needle 22. While pushing the endoscope 20 and outer balloon 2 and directing the guide wire toward the stomach side, the puncture needle 22 is detached from the inside of the balloon 2. The physiological saline or the like within the outer balloon 2 is sucked by means of the syringe 21 to cause this outer balloon 2 to contract, and the endoscope 20 is pulled back to the upper part of the esophagus. A dilator with a sheath (not shown) is inserted from the terminal end of the guide wire to expand the puncture side, with visual recognition by means of the endoscope 20. Then, only the dilator is removed to ensure a route to the inside of the esophagus. By virtue of the thus-ensured route, an appropriate catheter is subsequently inserted.

The site where the guide tube of the present invention is used and the method of such use can safely and reliably ensure a route for percutaneous approach to the inside of all the hollow organs (such as esophagus, stomach, bile duct, pancreatic duct, intestine, ureter and bladder), by appropriately changing or selecting the sizes of and materials for the endoscope 20, outer balloon 2, inner balloon 9 and puncture needle 22, and, additionally, guide wire, dilator and sheath used, in addition to the above-described method for forming a route for percutaneous approach from the cervical part to the esophagus.

In the meantime, the endoscope is inserted into/pulled out of the main body tube 1 which is a member constituting the guide tube of the present invention, as described above, and thus the main lumen 5 for endoscope insertion penetrates from its tip end to its rear end. In the case where the endoscopic operation such as suction is necessary in the treatment, a membrane-like seal part 4 provided with a slit or hole may sometimes be mounted at the rear end of the main lumen 5 in order to ensure the degree of a negative pressure at the tip end side. The hole or slit to be mounted is determined to have a dimension slightly smaller than that of the endoscope 20, and synthetic resins such as soft vinyl chloride resins, polyurethane resins and silicone rubbers are suitably used as the materials therefor. However, the usable materials are not limited to these examples.

Industrial Availability

The present invention is as described above, and the inventive guide tube is used, thereby making it possible to safely and reliability form a percutaneous route in all the hollow organs (such as esophagus, stomach, bile duct, pancreatic duct, intestine, ureter and bladder) for various purposes. Further, the procedures, which conventionally had to be performed with many hands in an operating room or the like because an X-ray imaging machine was used, is combined with an endoscope and an ultrasonic probe so that the procedures can be performed by two persons at a bed side.

Especially, an inner balloon has been provided to ensure a large puncture space (penetration depth of the puncture needle) as compared with that of the conventional balloon for puncture in the present invention. Thus, the present invention is quite useful in successfully performing the above bed-side procedures.

BRIEF DESCRIPTION OF INVENTION

EXPLANATION OF REFERENCE NUMERALS

Figure 1:
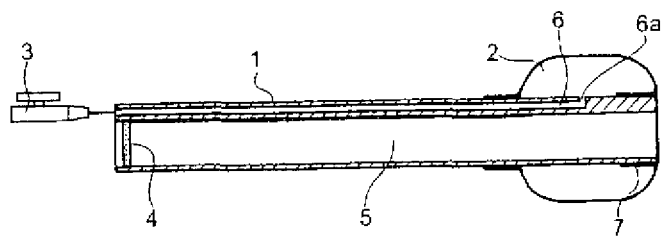
FIG. 1 is a sectional side view of a conventional guide tube.
Figure 2:
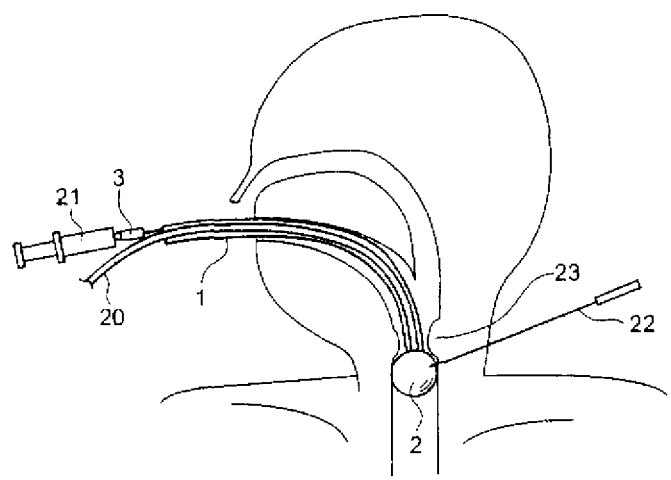
FIG. 2 is a schematical view showing a method for using the guide tube shown in FIG. 1.
Figure 3:
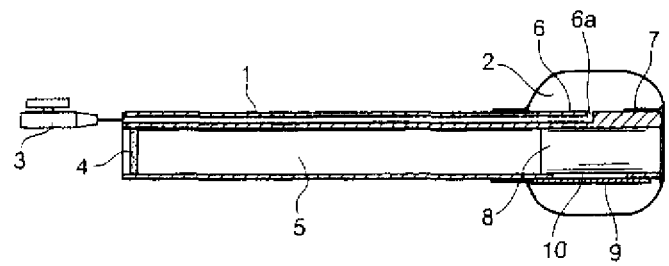
FIG. 3 shows a sectional side view of the guide tube as one Example of the present invention.
Figure 4:
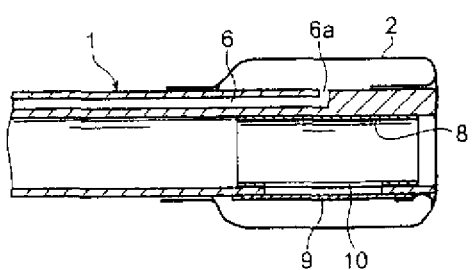
FIG. 4 is a sectional side view showing an enlarged tip end of the guide tube as one Example of the present invention.
Figure 5:
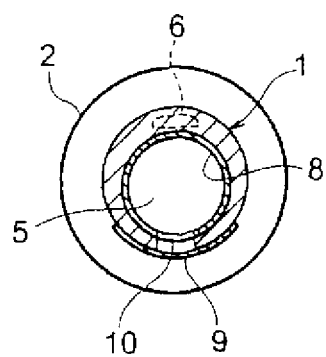
FIG. 5 is a right-side sectional view of FIG. 4.
Figure 6:
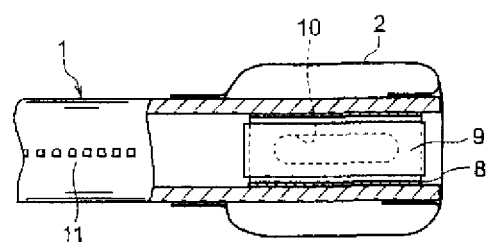
FIG. 6 is a flat sectional view of FIG. 4.
Figure 7:
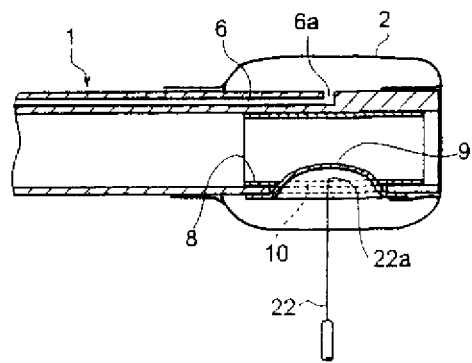
FIG. 7 is a sectional side view of an enlarged tip end part, showing the state where a balloon is punctured with a puncture needle when the guide tube as one Example of the present invention is inflated.
Figure 8:
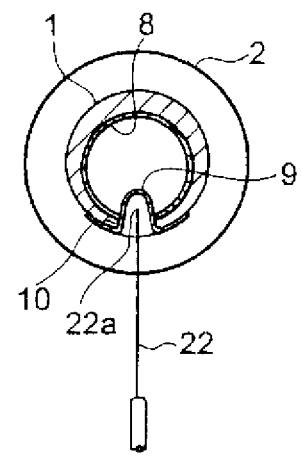
FIG. 8 is a right-side sectional view of FIG. 7.

1 Main body tube
2 Outer balloon
3 Connector
4 Membrane-like seal part
5 Main lumen for endoscope insertion
6 Sub lumen
7 Attachment part of outer balloon 2
8 Reinforcing pipe
9 Inner balloon
10 Elongate hole
11 Marking

The invention claimed is:

1. A guide tube equipped with a balloon for puncture, comprising:
 a main body tube equipped with a balloon on a main body tube tip end-side surface, the main body tube having:
 a main lumen for insertion of an endoscope, which penetrates from a rear end to the tip end-side; and
 a sub lumen brought in gas/liquid communication with the inside of the balloon,
 the main lumen being provided, at a main lumen rear end, with an endoscope insertion part, and
 the sub lumen being provided, at a sub lumen rear end, with connectors for inflating and contracting operations of the balloon,
 wherein the balloon on the tip end-side surface is used as an outer balloon,
 a needle through hole, through which a puncture needle passes, is formed in a wall surface of the main body tube located inside the outer balloon, the needle through hole is blocked air-tightly with an inflatable sheet material, and the inflatable sheet material is provided as an inner balloon, the inner balloon being so formed that, upon inflation of the outer balloon, the inner balloon inflates and projects from the needle through hole toward the inside of the main lumen due to internal pressure of the outer balloon, so that a tip end of the puncture needle can be pierced into an inflating and projecting part.

2. The guide tube equipped with a balloon for puncture according to claim 1, wherein the outer balloon and the inner balloon are formed of a same material.

3. The guide tube equipped with a balloon for puncture according to claim 1, wherein the needle through hole is formed into an elongate shape with a size of about 10 mm ×20 mm.

4. The guide tube equipped with a balloon for puncture according to claim 1, wherein a reinforcing pipe is mounted on an inner surface of the main lumen at the site where the needle through hole is provided.

5. The guide tube equipped with a balloon for puncture according to claim 1, wherein a marking for identifying the position of the needle through hole on an outer periphery of the main lumen is provided on a line along a length direction of the main body tube including the needle through hole provided in the wall of the main lumen of the main body tube.

6. The guide tube equipped with a balloon for puncture according to claim 1, wherein the outer balloon has the following material properties: a thickness of 0.01 mm to 1 mm, a tensile strength of 8 MPa to 25 MPa, a 100% modulus of 3 MPa to 6 MPa, an elongation of 300% to 460%, and a balloon internal pressure of 2.8 psi to 75 psi, and the inner balloon has material properties which are identical with those of the outer balloon, or has such material properties that the inner balloon is easier to inflate than the outer balloon.

7. The guide tube equipped with a balloon for puncture according to claim 1, wherein the main body tube has transparency ensuring visual recognition of the inside of the outer balloon from an endoscope.

8. The guide tube equipped with a balloon for puncture according to claim 1, wherein an outer balloon attachment part located at least at the tip end side in the main body tube is mounted to be arranged inside the outer balloon with respect to a longitudinal direction of the outer balloon.

9. The guide tube equipped with a balloon for puncture according to claim 1, wherein the endoscope insertion part provided at the rear end in the main lumen is equipped with a membrane seal member with a slit or a hole.

10. The guide tube equipped with a balloon for puncture according to claim 1, wherein said sheet material of the inner balloon extends along and parallel to an outer surface of said main lumen, and wherein upon said inflation of said outer balloon, the inner balloon projects inside the circumference of said main lumen and creates a cavity enabling the puncture needle to extend through said needle through hole and inside the circumference of said main lumen.

* * * * *

UNITED STATES PATENT AND TRADEMARK OFFICE
CERTIFICATE OF CORRECTION

PATENT NO.      : 8,486,100 B2
APPLICATION NO. : 12/747026
DATED           : July 16, 2013
INVENTOR(S)     : Oishi et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 294 days.

Signed and Sealed this
Eighth Day of September, 2015

Michelle K. Lee
*Director of the United States Patent and Trademark Office*